[19] United States Patent
Yip et al.

[11] Patent Number: 4,552,697
[45] Date of Patent: Nov. 12, 1985

[54] COMPOUND USEFUL IN DETECTING IONS AND METHOD OF PREPARING IT

[75] Inventors: Kin F. Yip; Steven C. Charlton, both of Elkhart, Ind.

[73] Assignee: Miles Laboratories, Inc., Elkhart, Ind.

[21] Appl. No.: 493,951

[22] Filed: May 12, 1983

[51] Int. Cl.⁴ .............................................. C07C 97/22
[52] U.S. Cl. ................................................ 260/396 N
[58] Field of Search .................................... 260/396 N

[56] References Cited

FOREIGN PATENT DOCUMENTS 639191 4/1962 Canada ........................... 260/396 N

OTHER PUBLICATIONS

H. D. Gibbs, *Chem. Review* (13), 1927, pp. 291–319.
D. Svobodova et al., *Mikrochemica Acta*, 1978, pp. 251–264.
*Chemical Abstract*, vol. 74, 1971, #4623f, Corbett "Benzoquinone imines".
*Chemical Abstract*, vol. 80, 1974, #119847y, Pelizzetti, "Kinetics of oxidative condensation of p-phenylene diamines with monohydrin phenols and naphthols".

Primary Examiner—Glennon H. Hollrah
Assistant Examiner—Raymond Covington
Attorney, Agent, or Firm—Edward H. Gorman, Jr.

[57] ABSTRACT

A novel compound is disclosed having the structure

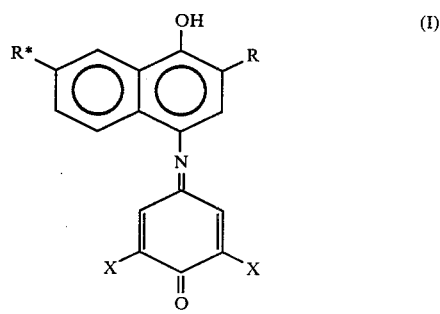

in which R is H or lower alkyl, R* is intermediate alkyl, and X is halogen or pseudohalogen. Also disclosed is a method for preparing the compound, the method including the steps of reacting (intermediate alkyl)benzene (I) with succinic anhydride to form (intermediate alkyl)-benzoylpropionic acid (II), successively reducing and dehydrating (II) to form 7-(intermediate alkyl)-1-tetralone (III), alkylating (III) to form 2-hydroxy(lower alkylidene)-7-(intermediate alkyl)-1-tetralone (IV), acrylating (IV) to form 2-acyloxy(lower alkylidene)-7-(intermediate alkyl)-1-tetralone (V), reacting (V) in the presence of an cycloalkene to form 7(intermediate alkyl)-2-(lower alkyl)-1-naphthol (VI), reacting (VI) with a 2,6-dihaloquinone-4-haloimide to form the compound (I), and isolating it.

8 Claims, No Drawings

COMPOUND USEFUL IN DETECTING IONS AND METHOD OF PREPARING IT

INTRODUCTION

The present invention relates to a novel compound useful in the measurement of ions, in particular ions in aqueous solution. Moreover, the novel compound is prepared by a novel process, and it is that part of the invention, the process, which enables the preparation of the compound.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function. Such conditions include oliguria, anuria, urinary obstruction and renal failure due to shock.

Needless to say, a quick, facile method for determining ion concentration would greatly enhance the state of these technologies, as well as any others where such rapid, accurate determinations would be beneficial. Thus, for example, if a medical laboratory technician could accurately measure the potassium or calcium level of a serum or whole blood sample in a matter of seconds or minutes, not only would such rapid results aid the physician in diagnosis, but also laboratory efficiency would increase manyfold. The present compound is the linchpin of such a test, being a reporter substance which, when present in a composition containing an ionophore for the ion to be detected, produces a detectable response to the presence of the ion.

BACKGROUND OF THE INVENTION

Prior to the present invention, phenolic imine compounds were prepared by the so-called Gibbs Reaction. H. D. Gibbs, *Chem. Review* 13, 291–319 (1927). See also D. Svobodova, et al., *Mikrochimica Acta*, pp. 251–264 (1978). These references, the contents of which are incorporated herein by reference, describe the coupling of phenols with imines in accordance with

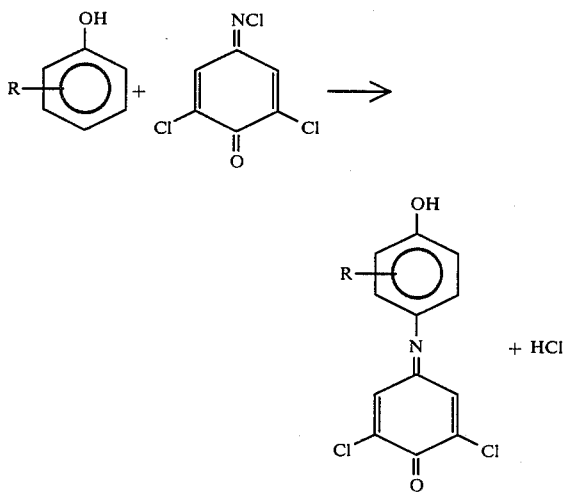

While such compounds are useful as reporter substances, the presently disclosed compounds are resistant to interference in ion determination caused by the presence of protein, such as albumin, in the test sample.

SUMMARY OF THE INVENTION

The present invention resides in the discovery of a novel compound having the structure

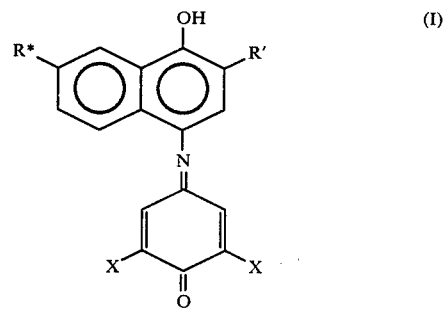

in which R' is H or lower alkyl, R* is intermediate alkyl and X is halogen or pseudohalogen. The invention additionally comprises a process for preparing (I), and which includes the steps of reacting an (intermediate alkyl)benzene (II) with succinic anhydride to form β-(intermediate alkyl)-benzoylpropionic acid (III), successively reducing and dehydrating (III) to form 7-(intermediate alkyl)-1-tetralone (IV), alkylating (IV) to form 2-hydroxy(lower alkylidene)-7-(intermediate alkyl)-1-tetralone (V), acylating (V) to form 2-acyloxy(-lower alkylidene)-7-(intermediate alkyl)-1-tetralone (VI), reacting (VI) in the presence of an cycloalkene to form 7-(intermediate alkyl)-2-(lower alkyl)-1-naphthol (VII), reacting (VII) with a 2,6-dihaloquinone-4-haloimide to form compound (I).

DEFINITIONS

Certain terms used in the present discussion should at this point be mentioned to assure that the reader is of the same mind as the author as to their respective meanings. Thus the following definitions are provided to clarify the scope of the present invention, and to enable its formulation and use.

4.1 The term "ionophore" includes molecules capable of selectively forming a complex with a particular ion to the substantial exclusion of others. For example the cyclic polypeptide valinomycin, binds selectively to potassium ions in solution to form a cationic complex. Also included in the term are coronands, cryptands and podands.

4.2 As used herein, "substantially nonpolar" is intended as meaning that quality of a substance not to exhibit a substantial dipole moment or electrical polarity. In particular, it includes nonionic substances, and substances which are dielectric.

4.3 The term "nonporous" is intended to mean substantially impervious to the flow of water. Thus a nonporous carrier matrix is one which substantially precludes the passage of water through it, one side to the other. For example, a polyvinyl chloride film would be considered for the purposes herein as being nonporous.

4.4 A "reporter substance" is a compound, such as that of the present invention, which is capable of interacting with an ionophore/ion complex to produce a color change or other detectable response. Thus, a reporter substance can be one which is relatively colorless in the non-ionized state, but which colors when in the presence of a complex of an ionophore and an ion.

4.5 By "interacting" is meant any coaction between a reporter substance and an ionophore/ion complex which leads to a detectable response. An example of the reporter substance interacting with the complex is in the case where the reporter is changed by the complex from a colorless to a colored state, such as in the case of 7-(n-decyl)-2-methyl-4-(3',5'-dichlorophen-4'-one)-indonaphth-1-ol.

4.6 The term "detectable response" is meant herein as a change in or occurrence of a parameter in a test means system which is capable of being perceived, either by direct observation or instrumentally, and which is a function of the presence of a specific ion in an aqueous test sample.

4.7 By the term "intermediate alkyl" as used herein is meant an alkyl group, substituted or unsubstituted, having from about 4 to about 12 carbon atoms. It includes normal and branched isomers. It may be unsubstituted or it may be substituted, provided any such substitution not interfere with the operation of the presently claimed test means or device in its capability to detect ions.

4.8 The term "lower alkyl", as used in the present disclosure includes an alkyl moiety, substituted or unsubstituted, containing about 1-4 carbon atoms. Included in the meaning of lower alkyl are methyl, ethyl, n-propyl, isopropyl, n-butyl, sec-butyl and tert-butyl. These may be unsubstituted, or they may be substituted provided any such substituents not interfere with the operation or functioning of the presently claimed test means or device in its capability to detect ions. "Lower alkylidene" is used in the same context as "lower alkyl", but designates an alkylene group (i.e., a divalent alkyl) having 1-4 carbon atoms. Thus, lower alkylidene includes methylene, ethylidene, n-propylidene, isopropylidene, n-butylidene, sec-butylidene and tert-butylidene.

4.9 By "pseudohalogen" is meant atoms or groups of atoms which, when attached to an unsaturated or aromatic ring system, affect the electrophilicity or nucleophilicity of the ring system, and/or have an ability to distribute an electrical charge through delocalization or resonance, in a fashion similar to the halogens. Thus, whereas halogen signifies Group VII atoms such as F, Cl, and I, pseudohalogens embrace such moieties as —CN, —SCN, —OCN, —N$_3$, —COR, —COOR, —CONHR, —CF$_3$, —CCl$_3$, —NO$_2$, —SO$_2$CF$_3$, —SO$_2$CH$_3$, and —SO$_2$C$_6$H$_4$CH$_3$, in which R is alkyl or aryl.

THE COMPOUND

The compound of the present invention, as stated supra, is one having the structure

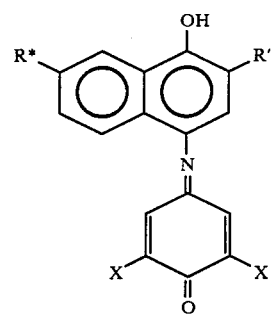

in which R* is an intermediate alkyl group, i.e., having 4-12 carbon atoms, X is halogen or pseudohalogen and R' is H or lower alkyl. Compounds such as these have been found to be especially resistant to possible interference in ion detection due to the presence of protein in the test sample, and thus render the test more sensitive and the results more reproducible than with certain other reporter substances. Preferred among these types of reporter substances is that in which R* is n-decyl and R is methyl.

USE OF THE INVENTION

The compound of the present invention (I) lends itself especially well to a test device for determining the presence of an ion in an aqueous test sample. Such a device comprises a test means affixed to one end of an elongated support member, the other end serving as a handle.

The test means comprises a carrier matrix incorporated with an ionophore and a reporter substance, i.e., compound (I). When an aqueous test sample contains an ion capable of specifically complexing with the ionophore, the ion can then enter the matrix, complex with the ionophore and interact with the reporter substance, thereby producing a detectable response.

The Carrier Matrix

The carrier matrix can be fabricated from a material which is both nonpolar and nonporous. Exemplary of such materials are films of such polymers as polyvinyl fluoride, polyvinyl chloride, vinyl chloride/vinyl acetate copolymer, vinyl chloridevinylidene chloride copolymer, vinyl chloride/vinyl acetate/vinyl alcohol terpolymer, vinylidene chloride/acrylonitrile copolymer, and polyurethane. Of course, many other polymeric materials would be suitable for use in the present invention, and the identification of such materials would be well within the skill of the art, given the present disclosure.

Other, nonpolymeric, materials would include ceramic substances, a painted substance (in which the paint layer would be the carrier matrix), glass-like substances, and other nonpolar materials.

These types of carrier matrices are ones which are not wetted by water, i.e., which preclude substantial penetration by the aqueous test sample. Moreover, it is intended that both the ionophore and reporter substance become substantially insoluble in the aqueous test sample due to their being entrapped within the carrier matrix. The requirement of non-porosity of the carrier matrix is to preclude substantial dissolution or leaching of ionophore or the reporter substance, as well as to prevent permeation by test sample components other than the ionic analyte.

Alternatively, the carrier matrix can be hydrophilic, the ionophore and reporter substance being incorporated in globules of a hydrophobic vehicle uniformly dispersed throughout the hydrophilic carrier matrix. In such a system the aqueous test sample has substantially unimpeded accessibility to the outer surface of the hydrophobic globules. The carrier matrix with which the globules are incorporated must be easily wettable by aqueous systems, i.e., hydrophilic.

Typical of some materials which display suitable hydrophilicity are gelatin, agarose, poly(vinyl alcohol), poly(propyleneimine), carrageenan, and alginic acid. These are water-soluble or water-wettable polymers which, in their dry state, exhibit a marked wettability by aqueous media.

Other, polymeric materials suitable for use include porous substances, such as paper and other cellulosic systems, sintered ceramic frits and similar porous, hydrophilic matrices, provided the integrity of the globules can be maintained. Thus, for example, a suitable carrier matrix is a combination of paper and gelatin. In this instance a filter paper pad can be impregnated with a stable emulsion of aqueous gelatin and the hydrophobic globules. Upon drying, the filter paper/gelatin carrier matrix is capable of preserving the integrity of the globules until the test means is put to its intended use.

The primary function of the hydrophobic vehicle is to isolate the ionophore and reporter substance from the aqueous test sample. Thus the vehicle can be a liquid or solid substance, so long as it possesses sufficient hydrophobicity to achieve the above-mentioned isolation of reagents from the test sample. Moreover, the vehicle must preclude substantial ionic penetration of the globule unless the ion is one capable of complexing with the ionophore.

Substances which are useful as hydrophobic vehicles include liquids which are simultaneously insoluble in water and capable of dissolving an ionophore and a reporter substance in sufficient concentration to provide a substantial response when in use. They must be relatively nonvolatile, i.e., having a boiling of at least about 150° C. Typical liquids which fall into this category are tricresylphosphate, 2-nitrophenyloctyl ether, 2-nitrophenylbutyl ether, dioctylphthalate, tris-2-ethylhexyl phosphate, di-2-ethylhexyl sebacate, and n-butyl acetyl ricinolate.

In addition to oils, and other liquid vehicles, it is likewise feasible to utilize finely divided particles (globules) of solid materials to contain and isolate the ionophore and reporter substance. Thus the vehicle can comprise hydrophobic materials such as organic polymers which are substantially nonporous and nonpolar. These include polyvinyl fluoride, polyvinyl chloride, vinyl chloride/vinyl acetate copolymer, vinyl chloride/vinylidene chloride copolymer, vinyl chloride/vinyl acetate/vinyl alcohol terpolymer, and vinylidene chloride/acrylonitrile copolymer.

Ionophores

The ionophore element of the test device is indeed a concept which is broad in scope, as characterized by the definition of the term in paragraph 4.1, supra. It includes multidentate cyclic compounds which contain donor atoms in their cyclic chains. Such multidentate cyclic compounds can be monocyclic or polycyclic. Alternatively, the ionophore can be an open chain containing donor atoms. Thus, included in the term are monocyclic systems which are ion-specific, termed coronands; polycyclic ion-specific compounds known as cryptands; and acyclic structures, known as podands, which are capable of selectively complexing with ions.

Coronands

The coronands are monocyclic compounds which contain donor atoms which are electron rich or deficient and which are capable of complexing with particular cations and anions because of their unique structures. Included in this term are the crown ethers in which the monocyclic chain contains oxygen as the donor atoms. Other coronands are compounds which contain an assortment of electron rich atoms such as oxygen, sulfur and nitrogen. Because of the unique sizes and geometries of particular coronands, they are adaptable to complexing with various ions to the substantial exclusion of others. In so complexing, the electron rich atoms, such as the oxygens in a crown ether, orient towards the electron deficient cation. The carbon atom segments of the chain are simultaneously projected in a direction outwards from the ion. Thus, the resultant complex is charged in the center but is hydrophobic at its perimeter.

Cryptands

The cryptands are the polycyclic analogues of the coronands. Accordingly, they include bicyclic and tricyclic multidentate compounds. In the cryptands, the cyclic arrangement of donor atoms is three dimensional in space, as opposed to the substantially planar configuration of the coronand. A cryptand is capable of virtually enveloping the ion in three dimensional fashion and, hence, is capable of strong bonds to the ion in forming the complex. Like in the coronands, the donor atoms can include such atoms as oxygen, nitrogen and sulfur.

Podands

Ions can also be selectively complexed with acyclic compounds. For example, a linear chain which contains a regular sequence of electron rich atoms such as oxygen has the capability of associating with positively charged ions to form complexes, not entirely unlike the coronands and cryptands. The main structural difference between podands and their cyclic analogues is the openness of the structure. Thus, podands can be subcategorized into monopodands, dipodands, tripodands, . . . . A monopodand, therefore, is a single organic chain containing donor atoms, a dipodand is two such chains attached to a central atom or group of atoms, and is capable of variable spacial orientation, and a tripodand is three such chains.

Specific Ionophores

Some of the ionophores which have been found to be especially useful with the test device are tabulated herein along with the cations with which they are capable of selectively complexing.

| Ionphore | Cation |
| --- | --- |
| Valinomycin | $K^+$ |
| 4,7,13,16,21-Pentaoxa-10,10-diaza-bicyclo[8,8,5]tricosane (Kryptofix 221) | $Na^+$ |
| 4,7,13,16,21,24-Hexaoxa-1,10-diaza-bicyclo[8,8,8]hexacosane (Kryptofix 222) | $K^+$ |
| 4,7,13,18-Tetraoxa-1,10-diaza-bicyclo[8,5,5]eicosane (Kryptofix 211) | $Li^+$ |
| 12-Crown-4 | $Li^+$ |
| 15-Crown-5 | $Na^+, K^+$ |
| 18-Crown-6 | $K^+$ |
| Dibenzo-18-crown-6 | $K^+$ |

| -continued | |
|---|---|
| Ionphore | Cation |
| Dicyclohexano-18-crown-6 | K+ |

Kryptofix is a registered trademark of E. Merck, Darmstast, Germany

The Reporter Substance

Given the presence of the ion of interest in the test solution, it is the reporter substance, i.e., compound (I), which provides the detectable response as a result of its interacting with the ionophore/ion complex. The reporter substance is capable of producing a detectable response when triggered by the complex. Thus, it can be seen that when no analyte ion is present the reporter substance remains dormant; no detectable response is observed. Alternatively, when the particular ion under surveillance is present, it is enabled by the ionophore to enter the carrier matrix to form a complex, which complex interacts with the compound of the present invention and induces it to undergo a detectable change.

The Support Member

The test means described above can be used by itself or it can be mounted at one end of an elongated support member, the other end serving as a handle. Such a test device can be held at the handle end, while the other end bearing the test means is contacted with the test sample.

Useful materials for the support member include films of a myriad of plastics or polymers. Examples include such polymeric materials as cellulose acetate, polyethylene tetephthalate, polycarbonates and polystyrene. The support can be opaque or it can transmit light or other energy. Preferred supports include transparent materials capable of transmitting electromagnetic radiation of a wavelength in the range of about 200 nanometers (nm) to 900 nm. It may also be desirable to have a support that transmits one or more narrow wavelength bands and is opaque to adjacent wavelength bands. This could be accomplished, for example, by impregnating or coating the support with one or more colorants having suitable absorption characteristics.

The test device is prepared by affixing a small rectangle of the test means, i.e., a carrier matrix incorporated with an ionophore, the reporter substance and possibly other ingredients, to an elongated support member having an upper substantially flat face, such as an oblong piece of polystyrene film. The test means piece is affixed to the flat face at one end, leaving the other end of the polystyrene to serve as a convenient handle.

The test means can be affixed by any means compatible with the intended use. A preferred method is by using a double faced adhesive tape between the test means square and the support member. One such tape is known as Double Stick®, available from 3M Company.

Assaying for Ions in a Sample

The test means and device of the present invention can be adapted for use in carrying out a wide variety of chemical analyses, not only in the field of clinical chemistry, but in chemical research and chemical process control laboratories. They are well suited for use in clinical testing of body fluids such as blood, blood serum and urine, since in this work a large number of repetitive tests are frequently conducted, and test results are often needed a very short time after the sample is taken. In the field of blood analysis, for example, the invention can be adapted for use in carrying out quantitative or semiquantitative analysis for many of the ionic blood components of clinical interest.

The test means (and test device) is used by contacting it with the test sample, and observing a detectable response. If the ion under analysis is present in the test sample, the complex of ionophore and ion will interact with the reporter substance and a detectable response will appear. Included in techniques useful in observing the detectable response are direct visual observation, reflectance spectrophotometry, absorption spectrophotometry and light transmission measurements.

When the test sample is blood serum, transmission techniques can be used to detect and quantify the presence of any reaction products, the formation of which serves as the detectable response. In this case radiant energy, such as ultraviolet, visible or infrared radiation, is directed onto one surface of the test means and the output of that energy from the opposite surface is measured. Generally, electromagnetic radiation in the range of from about 200 to about 900 nm has been found useful for such measurements, although any radiation permeating the test means and which is capable of signifying the occurrence or extent of the response can be used.

Various calibration techniques are applicable as a control for the analysis. For example, a sample of analyte standard solution can be applied to a separate test means as a comparison or to permit the use of differential measurements in the analysis.

EXAMPLES

The following Examples are provided to further assist the reader in making and using the present invention. Thus, preferred embodiments are described in experimental detail and analyzed as to the results. The Examples are meant to be illustrative only, and are in no way intended as limiting the scope of the invention described and claimed herein.

7.1 Preparation of 7-(n-Decyl)-2-methyl-4-(3',5'-dichlorophen-4'-one)-indonaphthl-1-ol The captioned compound (hereafter 7-decyl-MED-PIN) was prepared in accordance with the following procedure. The reaction pathway is depicted in the following sequence, in which R* is n-decyl.

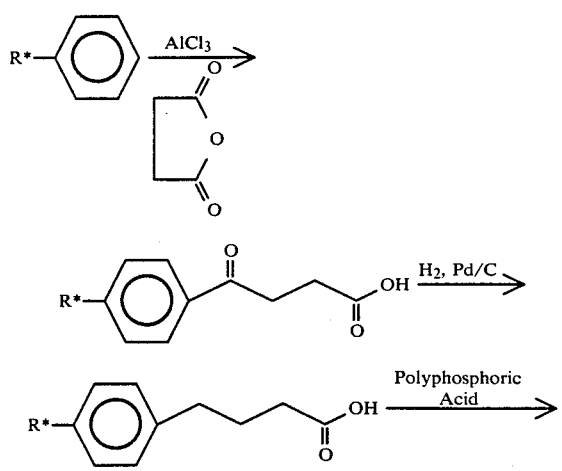

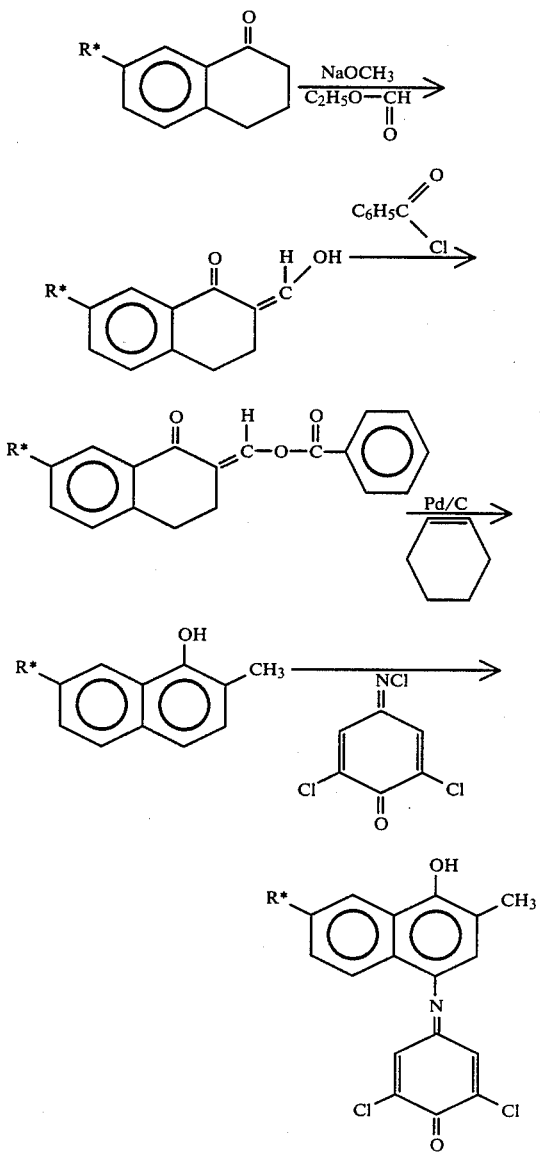

Preparation of β-(p-n-Decyl)-benzoyl Propionic Acid

A mixture of 26.2 grams (g) phenyl-n-decane (1.2 mole), 120 g succinic anhydride (1.2 mole) and 360 mililiters (mL) nitroethane in an 5 liter (L) three-necked flask equipped with HCl outlet and mechanical stirrer was cooled to 0° C. in an ice-bath. To this mixture 360 g AlCl₃ (2.7 moles) was added slowly over ½ hour with stirring. Evolution of HCl was observed when about half of the AlCl₃ was added. After the addition, the ice bath was removed, the reaction mixture was allowed to stand at room temperature (RT) for 5 minutes. The mixture was then heated over a steam bath. The heating and stirring were continued until the vigorous evolution of HCl ceased (about 30 minutes). The reaction was cooled in an ice bath while 2 L of ice water was added, followed by 600 mL of concentrated HCl. This was stirred at RT for 2 hours until all the dark brown solid was hydrolyzed. The insoluble product was recovered by filtration. The solid was then recrystallized twice with acetic acid (250 mL each time) to give about 320 g (85% yield) of product (dried in vaccuum over KOH). TLC: Rf 0.43 in 1:1 (v/v) ethylacetate:toluene (silica gel plate).

Analysis: Calculated for $C_{20}H_{30}O_3$: C, 75.42; H, 9.50. Found: C, 76.02; H, 9.89.

Preparation of 4-(p-n-decyl)-phenyl-butyric Acid

Twenty grams of Pd/C (palladium-saturated carbon obtained from Aldrich Chemical Co., catalogue No. 20,569-9) and β-(p-n-decyl)-benzoyl-propionic acid (150 g 0.47 moles) were mixed with acetic acid (350 mL) in a 1 L Paar bomb. The reaction was started at 50 psi H₂ pressure and 50° C. A sudden increase in temperature accompanied by a drop in H₂ volume was observed. Thin layer chromatography of the reaction mixture indicated complete reaction. The catalyst was removed by glass fiber filtration while hot. The filtrate was allowed to crystallize at RT. The crystalline product was recovered by filtration. A second crop of product which formed after the filtrate was chilled was also recovered. The total yield was 100 g (68%) after drying under a vacuum over KOH. Melting point: 67°–69° C.

TLC: Rf 0.68 in 1:1 (v/v) EtOAc: toluene (silica gel plate)

Analysis Caluclated for $C_{20}H_{32}O_2$: C, 78.90; H, 10.50. Found: C, 78.39; H, 10.70.

Preparation of 7-n-Decyl-1-tetralone

A mixture of 4-(p-n-decyl)-phenyl butyric acid (30 g, 98.7 mmoles) and polyphosphoric acid (150 g) was heated in an oil bath until all solid was melted. The heating was elevated to 150° C. (internal temp.) and the mixture was stirred vigorously for 30 minutes. The reaction was then cooled to RT and treated with 300 mL ice water and 150 mL ethyl ether. After the mixture was stirred for 30 minutes at RT, the layer was separated and washed twice with 150 mL ethyl ether. The combined organic phases were washed with 150 mL saturated aqueous NaCl. Ether was removed by evaporation and the residue was distilled on a Kügelrohr distillation apparatus (Aldrich Chemical Co.). The product had a boiling point of 190°–200° C./0.1 mm Hg. The yield was 11 g (39%) of pale yellow oil.

TLC: Rf-0.34 in toluene (silica gel plates)

Analysis Calculated for: $C_{20}H_{30}O$: C, 83.90; H, 10.70. Found: C, 85.63; H, 10.83.

Preparation of 2-Hydroxymethylene-7-n-decyl-1-tetralone

A mixture of sodium methoxide (5.4 g, 40.5 mmoles), ethyl formate 7.4 g, 100 mmoles) and 100 mL dry toluene was cooled in an ice bath under inert atmosphere (N₂ or Argon). A solution of 7-n-decyl-1-tetralone (11.5 g, 40 mmoles) in 100 mL dry toluene was added with rapid stirring. The ice bath was removed and the reaction was stirred at RT for 4 hours. The reaction was treated with 100 mL water and 100 l mL 6N HCl. The organic layer was separated and washed twice with 50 mL saturated NaCl, dried over anhydrous Na₂SO₄, filtered and evaporated to remove all the toluene. The oily residue was used for the next reaction without further purification.

TLC: Rf=0.56 in toluene (silica gel plates), the spot turned dark-brown after spray with 5% FeCl₃ solution.

Preparation of 2-Benzoyloxymethylene-7-n-decyl-1-tetralone

The oily residue from the previous reaction step was mixed with dry pyridine (120 mL). The solution was stirred under nitrogen at 0° C. (ice bath). The solution was treated with 30 mL of benzoyl chloride After the addition of the benzoyl chloride, insoluble pyridinium chloride was observed in the mixture. The reaction was stirred at RT for two hours. The product was poured into ice water (400 mL) with vigorous stirring. The light cream color solid was recovered by filtration, and washed well with cold water. The slightly wet solid was recrystallized from hot absolute ethanol (120 mL). White solid (14 g, 87% yield based on the 7-n-decyl-1-tetralone) was recovered. The melting point was 64°–66° C.

TLC: Rf 0.40 in toluene (silica gel plates)

Analysis Calculated for: $C_{28}H_{34}O_3$: C, 80.34; H, 8.19. Found: C, 80.05; H, 8.27.

Preparation of 7-n-Decyl-2-methyl-1-naphthol

To a mixture of 2-benzoyloxymethylene-7-n-decyl-1-tetralone (14 g, 33.5 mmoles) and Pd/C (3.5 g) under inert atmosphere was added cyclohexene (175 mL). The mixture was heated to reflux while maintaining the inert atmosphere. The conversion of starting material to product was determined by TLC after 3 hours. After all the starting material reacted, the mixture was cooled down to RT. The catalyst was removed by filtration and washed twice with 50 mL hot toluene. The combined filtrate was evaporated to a small volume. The product was purified with a Prep-500 silica gel column (a high pressure silica gel preparative column, obtained from Waters Association, Milford, MA). Toluene was used as the mobile phase. The product fractions were pooled and evaporated to dryness under vacuum overnight. Cream white solid (9.0 g; 90% yield) was recovered. The melting point was 65°–67° C.

TLC: Rf=0.65 in toluene (silica gel plates). Pink color developed when the product spot was irradiated with short UV light.

Analysis calculated for: $C_{21}H_{30}O$: C, 84.50; H, 10.13. Found: C, 84.49; H, 10.72.

Preparation of 7-n-Decyl-2-methyl-4-(3',5'-dichlorophen-4'-one)-indonaphth-1-ol 7-n-Decyl-2-methyl-1-naphthol (4.5 g, 15.1 mmoles) and 2,6-dichloroquinone-4-chloroimide (3.0 g, 14.3 mmoles) were dissolved in acetone (150 mL). The solution was treated with 700 mL potassium carbonate solution (0.1M, pH=10.0) The solution was stirred vigorously at RT for 10 min. The pH of the reaction mixture was adjusted to 2.8 with 1.0N HCl. The mixture was stirred for 15 minutes. The red solid was recovered by filtration and washed well with water. The solid was dissolved in toluene and filtered with glass fiber paper to remove any insoluble materials. The filtrate was concentrated and purified with a Prep-500 silica gel column, toluene as the mobile phase. Product fractions were pooled and evaporated to dryness. The residue was crystallized with n-hexane (100 mL) to give product (3.9 g, 58% yield).

TLC; Rf=0.26 in toluene (silica gel plates). The brown color spot turned purple-blue after being treated with 0.1N NaOH on the plates.

Analysis Calculated for: $C_{27}H_{31}NO_2Cl_2$: C, 68.64; H, 6.57; N, 2.97. Found: C, 68.88; H, 6.85; N, 2.97.

7.2 Potassium Test Using Naphtho-15-crown-5 as Ionophore

An acetone mixture was prepared containing 10.8 mg (milligrams) 7-decyl-MEDPIN and 24 mg naphtho-15-crown-5 (2,3,5,6,8,9,11,12-octahydronaphtho[2,3-b]-1,4,7,10,13-pentaoxacyclopentadecane). Solvent was removed under a stream of nitrogen gas. Then dried solids were combined with 4 g of a film solution comprising 70% by weight cyclohexanone, 12% by weight vinyl chloride/polyvinylidene copolymer, 18% by weight diethyl phthalate (a plasticizer), and 60 ($\mu$L) Triton X-100 (a 1% weight solution of nonionic detergent in acetone; available from Rohm and Haas, Co.). The mixture was homogenized on a vortex mixer, and then spread into a thin film on a piece of KODAR cyclohexanone/dimethylene terephthalate copolymer channeled plastic film (Lustro Co.) using a doctor blade having a 10 mil (0.01 inch) gap. The dried film had a thickness of about 3 mils.

The test means was evaluated with aqueous test samples containing varios KCl concentrations. Each sample was 15.56 mM NaCl and 88.89 CAPS buffer [3(cyclohexylamino)-propanesulfonic acid] and was adjusted to pH 10 with LiOH. The respective KCl concentrations were 0, 0.33, 0.67 and 1.0 mM.

The evaluations were conducted by innoculating a section of the test means film with 40 microliters ($\mu$L) of test sample and the change in reflectance monitored for one minute in a SERALYZER ® reflectance Photometer (Ames Division of Miles Laboratories, Inc.).

The reflectance values (R) were converted to (K/S) in accordance with $$(K/S) = (1-R)^2/2R^2$$

in which R is the fraction of reflectance from the test device, K is a constant, and S is the light scattering coefficient of the particular reflecting medium. The above equation is a simplified form of the well-known Kubelka-Munk equation (See Gustav Kortüm, "Reflectance Spectroscopy", pp. 106–111, Springer Verlaz, New York (1969)). The data is tabulated below as (K/S) with respect to time.

| [K+] mM | (K/S) second$^{-1}$ |
|---|---|
| 0 | 0.001151 |
| 0.33 | 0.007679 |
| 0.67 | 0.01295 |
| 1.0 | 0.01909 |

As can be seen from the table, rate of change in (K/S) with time varies in accordance with potassium concentration.

7.3 Potassium Test Means Using Naphtho-15-crown-5 and Valinomycin as Ionophores A test means film was prepared and evaluated as in example 7.2 except that 6 mg of the naphtho-15-crown-5 was replaced by 6 mg valinomycin. The data is reported in the following table:

| [K+] mM | (K/S) second$^{-1}$ |
|---|---|
| 0 | 0.001182 |
| 0.33 | 0.007554 |

| [K+] mM | (K/S) second$^{-1}$ |
|---|---|
| 0.67 | 0.01331 |
| 1.0 | 0.01857 |

The data shows a direct correlation between potassium concentration and rate of change of (K/S).

7.4 Potassium Test Means Using Equal Amounts of Naphtho-15-crown-5 and Valinomycin as Ionophores A test means film was prepared and evaluated as in Example 7.2 except that 12 mg of naphtho-15-crown-5 was replaced by 12 mg valinomycin. The data is reported in the following table:

| [K+] mM | (K/S) second$^{-1}$ |
|---|---|
| 0 | 0.0007449 |
| 0.33 | 0.008314 |
| 0.67 | 0.01251 |
| 1.0 | 0.01898 |

The data shows a direct correlation between potassium concentration and rate of change of (K/S).

7.5 Potassium Test Means Using Valinomycin as Ionophore

A test means was prepared and evaluated as in Example 7.2 except that the amount of 7-decyl-MEDPIN was 5.4 mg, the ratio of vinyl chloride/vinylidene chloride copolymer to diethylphthalate was adjusted to 8.55:21.45 by weight, and the naphtho-15-crown-5 was replaced by 12 mg valinomycin.

The aqueous test samples contained KCl at concentrations of 0, 0.33, 0.67, 1.0, 2.0 and 3.0 mM. In addition, each solution contained 46.67 mM NaCl, 66.67 mM CAPS and was titrated to pH 10 with LiOH.

The reflectance data is reported in the following table:

| [K+] mM | (K/S) second$^{-1}$ |
|---|---|
| 0 | 0.001008 |
| 0.33 | 0.01090 |
| 0.67 | 0.01787 |
| 1.0 | 0.02872 |
| 2.0 | 0.04321 |
| 3.0 | 0.05330 |

As can be seen from the data, the test means exhibited a direct correlation between potassium concentration and the rate of change of (K/S) with time.

7.6 Potassium Test Means Using Dipentyl Phthalate as Plasticizer

A test means film was prepared and evaluated as in Example 7.2 except that the diethyl phthalate was replaced by an equal weight of dipentyl phthalate.

Aqueous test samples were as in Example 7.5 and contained KCl as indicated in the table of data below:

| [K+] mM | (K/S) second$^{-1}$ |
|---|---|
| 0 | 0.0005070 |
| 0.33 | 0.004041 |
| 0.67 | 0.007020 |
| 1.5 | 0.01391 |
| 3.0 | 0.02195 |

The data shows a direct correlation between potassium concentration and the rate of change of (K/S) with time.

7.7 Sodium Test Means

A solution of 10.8 mg 7-decyl-MEDPIN in acetone and a solution of 5 mg sodium Ligand I [N,N',N''-triheptyl-N,N',N''-trimethyl-4,4',4''-propylidentris-3-oxabutyramide] in tetrahydrofuran (THF) were mixed and the solvents removed under a stream of nitrogen. To the dried solids was added 0.5 g of a film solution. The latter was 70% by weight cylohexanone, 8.55% by weight of vinylchloride/vinylidene chloride copolymer, and 21.45% by weight dipentyl phthalate. The mixture was homogenized on a vortex mixer and the homogenate spread into a film on a piece of KODAR film using a 10 mil doctor blade. The dried film had a thickness of about 3 mils.

Aqueous sodium test samples were prepared for evaluating the test means. Each contained 88.98 mM CAPS and KOH was added to adjust the pH to 10. Samples were prepared containing 0, 11,11 mM and 22.22 mM NaCl, respectively.

To evaluate the ability of the test means to detect sodium, 40 μL of a test sample was applied to a section of the test means film and reflectance at 640 nm was monitored over 2 minutes in a SERALYZER reflectance photometer. Reflectance values were converted to (K/S) values as in Example 7.2. The rate of change of (K/S) with time and respective sodium concentrations are tabulated below:

| [Na+] mM | (K/S) second$^{-1}$ |
|---|---|
| 0 | 0.001459 |
| 11.11 | 0.003148 |
| 22.22 | 0.004354 |

The data shows a direct correlation between sodium concentration and the rate of change of (K/S) with time.

What is claimed is:

1. A compound having the structure

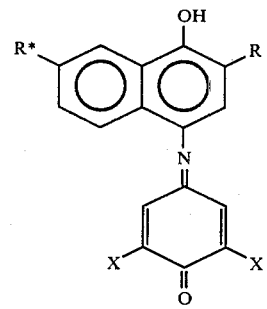

in which R is H or lower alkyl, R* is intermediate alkyl, and X is halogen or pseudohalogen.

2. The compound of claim 1 in which R* is n-decyl.
3. The compound of claim 2 in which R is methyl.
4. The compound of claim 3 in which X is chlorine.

5. A method for preparing the compound of claim 1, the method including the steps of reacting (intermediate alkyl)benzene (I) with succinic anhydride to form (intermediate alkyl)benzoylpropionic acid (II), successively reducing and dehydrating (II) to form 7-(intermediate alkyl)-1-tetralone (III), alkylating (III) to form 2-hydroxy(lower alkylidene)-7-(intermediate alkyl)-1-tetralone (IV), acylating (IV) to form 2-acyloxy(lower alkylidene)-7-(intermediate alkyl)-1-tetralone (V), reacting (V) in the presence of an cycloalkene to form 7-(intermediate alkyl)-2-(lower alkyl)-1-naphthol (VI), reacting (VI) with a 2,6-dihaloquinone-4-haloimide (VII) to form the compound of claim 1, and isolating the compound of claim 1.

6. The method of claim 5 in which (I) is n-decylbenzene.

7. The method of claim 6 in which the alkylating step is performed so as to produce 2-hydroxylmethylidene-7-(intermediate alkyl)-1-tetralone.

8. The method of claim 7 in which VIII is 2,6-dichloroquinone-4-chloroimide.

* * * * *